United States Patent [19]

Hansen

[11] Patent Number: 5,115,815
[45] Date of Patent: May 26, 1992

[54] OPHTHERMOMETRY: A METHOD OF MEASURING EYE TEMPERATURE FOR DIAGNOSIS AND SURGERY

[76] Inventor: Donald H. Hansen, 3923 Main, Davenport, Iowa 52803

[21] Appl. No.: 584,520

[22] Filed: Sep. 18, 1990

[51] Int. Cl.⁵ .......................... A61B 5/00; G01K 5/22
[52] U.S. Cl. .................... 128/664; 128/736; 374/121
[58] Field of Search ............... 128/664, 736; 250/330–334, 349; 374/124, 137, 121; 351/200, 221

[56] References Cited

U.S. PATENT DOCUMENTS

| | | | |
|---|---|---|---|
| 4,393,366 | 7/1983 | Hill | 382/2 |
| 4,494,881 | 1/1985 | Everest | 374/124 |
| 4,797,840 | 1/1989 | Fraden | 364/557 |
| 5,025,785 | 1/1991 | Weiss | 128/633 |

OTHER PUBLICATIONS

Mohr, Fredrick W. et al., "Thermal Angiography—A New Method . . . Surgery", *Surgical Forum*, 1987, pp. 208–210.

*Primary Examiner*—William E. Kamm
*Assistant Examiner*—Kevin Pontius
*Attorney, Agent, or Firm*—Robert O. Richardson

[57] ABSTRACT

The use of ophthermometers in a new field of ophthermology in the passive detection of thermal discrepance in the eyes of a person and its relation to health impairment and/or alcohol and drug abuse. Ophthermology has many uses. It can be used to initially establish a baseline or normal temperature for reference in identifying future eye problems. Readings can be taken from the pupil iris area or the white of the eye from the optic nerve to the cornea. Taking eye temperature before eye surgery can determine whether blood flow is adequate to permit surgery. Eye surgery can be monitored to determine the extent surgical wounds have healed and when the cease medication. Eye temperature readings can determine the fit of contact lenses, especially in fitting abnormal distorted corneas. Eye socket temperature can be measured to detect infection after traume of eye removal. Eye temperature differential can indicate reduced carotid flow and early detection of risk of stroke. Temperature readings assist in determining the effeciency of drug therapy. They also indicate impairment from alcohol and/or drugs. Intensive research and development of infrared thermography instruments have provided accurate, rapid, stable and repeatable readings that are relatively insensitive to user technique, making eye temperature patterns and data a part of accepted diagnostic procedures.

6 Claims, 1 Drawing Sheet

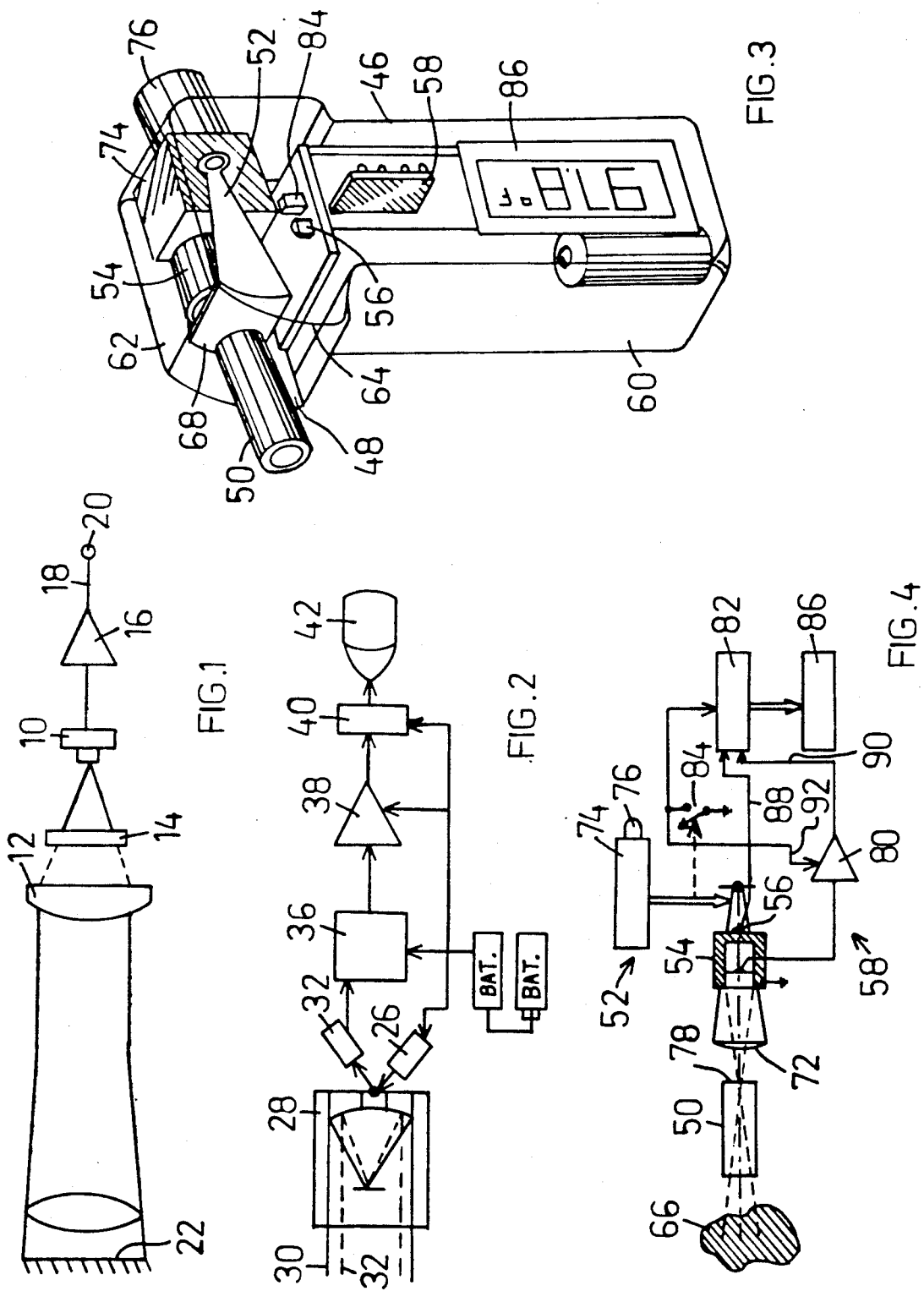

OPHTHERMOMETRY: A METHOD OF MEASURING EYE TEMPERATURE FOR DIAGNOSIS AND SURGERY

BACKGROUND OF THE PRESENT INVENTION

Strokes are the third leading killer of adults in this nation after cancer and heart disease. Half the survivors suffer permanent incapacitating disabilities. Over 40 percent of the patients in chronic care are stroke victims, many destined to spend their lives in such a facility despite intensive rehabilitative efforts. Arteriosclerotic disease of the extracranial carotid arterial complex, the arteries to the skull from the aorta which are the principal blood suppliers to the head and neck, is responsible for almost half of all strokes. If individuals at high risk for stroke can be more easily identified, preventive treatment can be initiated since the extracranial carotid artery is surgically accessible.

Noninvasive testing of the extracranial carotid complex has become a widely accepted method of patient screening for carotid stenosis or "narrowing of the orifice." Because these outpatient tests have a high degree of accuracy, a physician can use them to identify patients with significant carotid stenosis and refer the patient to a hospital for angiography and appropriate treatment.

In the past decade, improved medical and surgical methods of stroke prevention have emerged. Noninvasive diagnostic tests have achieved a degree of accuracy which justifies their acceptance as indicators of individuals at risk for stroke. No patient should be evaluated by only one noninvasive test, however, as each test has strengths and liabilities. A battery of tests best provides an indication of the patient's risk of stroke.

Ocular pneumoplethysmography (OPG-Gee) measures the pressure of the ophthalmic artery, the first major branch of the internal carotid artery. A disparity between ophthalmic artery and brachial artery (main artery of the arm) pressures provides indirect evidence of stenosis. OPG-Gee is a safe noninvasive test which accurately identifies patients with hemodynamically significant carotid stenosis.

Carotid phonoangiography (CPA) enables the examiner to analyze sounds emanating from blood vessels. A microphone is placed at various positions on the neck over the cervical carotid complex. In normal blood flow the CPA tracing will show heart sounds with no high frequencies. However, when laminar blood flow breaks down into turbulent flow, bruits or arterial origin sounds can be detected. Turbulence leads to artery pressure fluctuations causing the vessel wall to vibrate. These bruits can be heard on the skin surface through CPA and recorded audibly and graphically.

Thermography is a noninvasive test which depicts the body's infrared energy in a visible format. A thermograph detects and collects infrared radiations from the skin. Thermographic instruments have been used increasingly to diagnose cerebrovascular disease. Thermographic evaluation of the extracranial carotid complex is quite accurate in identifying individuals with high stroke risk.

While skin temperature can be affected by ambient temperature, humidity, air flow, and radiation, subcutaneous blood flow in the carotid complex is unaffected by external stimuli, an important factor in facial thermograms. While most of the face is nourished by the external carotid arteries, the eye orbits and surrounding tissues receive blood primarily from the internal carotid arteries. A normal facial thermogram shows temperature symmetry in areas supplied by the left and right, internal and external carotid arteries. A color scale and a calibrated temperature source have been developed to define specific temperatures in these various areas. Internal carotid stenosis, resulting in reduced blood flow to the eye, typically causes a significant ipsilateral decrease in periorbital tissue temperatures. Thermography detects this temperature decrease, generating an abnormal heat pattern. Successful endarterectomy results in a resumed blood flow through the internal carotid artery which is demonstrated by temperature symmetry in subsequent facial thermograms.

Ultrasound is an important noninvasive diagnostic tool to evaluate blood flow in the carotid complex. Pulse-echo ultrasonography uses high frequency signals to identify blood vessel walls and indicate stenosis. However, calcific plaque may absorb ultrasound waves and atherosclerotic plaque may have acoustic qualities similar to blood, thus escaping detection.

Combining the pulse-echo system with Doppler ultrasound does allow analysis of both vascular anatomy and blood flow. Periorbital Doppler Ultrasonagraphy detects blood flow direction in the terminal branches of the ophthalmic artery. In addition, this test measures flow changes in response to compression of selected branches of the external carotid artery. The beam from the Doppler instrument strikes moving blood cells and is reflected; the Doppler shift is proportional to blood velocity. Increased blood flow velocity through an area of stenosis has a corresponding increase in the pitch of the Doppler signal. Incoming information on blood flow velocity can be presented for audio, wave-form, and image analysis.

Not only has noninvasive infrared thermography been used to identify patients with a high risk of stroke, its measurement of the temperatures of parts of the body provides indications of various diseases and problems and the patient's physical condition. Unusual temperature patterns on the surface of the skin may be an indication of infection, disease, compromise of peripheral or arterial circulation, inflammation due to sprains or arthritis, vasodilation due to regional block or a drug regimen, acute venous thromboses, or exposure to the environment.

SUMMARY OF PRESENT INVENTION

Infrared thermography instruments have been improved through intensive research and development since temperature patterns and data have become part of accepted diagnostic procedures. Initially, such devices were difficult to properly attach to the body; the sensor took a significant length of time to adjust to the body surface temperature; they were prone to low readings when the surface thermal connection was inadequate. Properly aiming the device at the body target was also a problem. Now, however, rapid reading, infrared, accurately aimed thermometers make clinical readings of body surface temperatures practical. Infrared thermometry is fast, stable, repeatable and relatively insensitive to user technique.

The present invention expands the use of infrared thermography to ophthermology and as a tool for detecting suspected alcohol and/or drug abuse. With the present invention, an official may scan the eyes of a potential violator and obtain evidence of "probable cause" to justify further testing such as urine sampling to indicate possible use of illegal drugs and/or intoxicants for use in court proceedings. Combining a test for horizontal gaze nystagmus (constant, involuntary, cyclical eye movement caused by abuse of stimulants) and infrared ophthermology into one instrument, 90% accuracy can be achieved in less than one minute to determine whether a subject could be under the influence of alcohol and/or drugs.

Ocular thermology or ophthermology has many uses. Any patient can be initially tested to establish a baseline or normal temperature for reference in identifying future eye problems. Readings can be taken both frontally (pupil iris area) or sclerally (the white of the eye from the optic nerve to the cornea). Taking eye temperature before eye surgery can determine whether blood flow is adequate to permit the surgery, such as cataract removal, for example, or whether an adverse blood flow should be further explored and a discovered impairment collected before resorting to the initially planned surgery. Ophthermology can also be used as a monitor after eye surgery to assess the extent surgical wounds have healed and when to cease medication. Using eye temperature readings before and after fitting a patient with contact lenses can determine the fit of the lenses. Ophthermology can also be used to fit abnormal distorted corneas with cosmetic contact lenses. After the trauma of eye removal, the eye socket temperature can be measured to detect infection. Significantly different eye temperatures is a possible indicator of reduced carotid flow, leading to early detection of the risk of stroke. Eye tumors can also cause a variance in eye temperatures. Pain in one or both eyes can be monitored through temperature readings which can assist in determining the effeciency of drug therapy.

Patients can understand the concept of eye temperature as a diagnostic and screening tool which tends to reduce anxieties and result in fewer missed or cancelled appointments. This builds confidence in the doctor while the eye temperature measurement can actually be delegated to optometric assistants due to the speed, simplicity of use, and accuracy of the invention.

The instrument also has applicability as a health and safety screening device in the workplace. Employees whose impairment from alcohol and/or drugs would endanger the safety of the public or fellow workers can be tested as they enter the workplace.

The practice of ophthermology is advanced by a recently developed light-weight handheld unit which can be used by police officers, school and factory health personnel, sports officials, and company officials in sensitive industries such as transportation. This system combines accurate sensitive electronics which can print the results of the test on a strip chart printer attached to the instrument. It documents the known physiological effects of stimulants, cocaine, phencyclidine (Angel Dust or PCP), hallucinogens such as LSD, marijuana, inhalants, and depressants such as alcohol and narcotics.

Test results can be recorded without invading an individual's privacy; the device is completely noninvasive. The unit can be used day or night in any temperature and weather condition. An experienced trained operator can produce a written record of the test in one minute. A built-in voice activated recorder can be attached to the instrument to further document the test. This recording synchronized with the stripchart provides a full history of each test which can be quickly evaluated to determine the need for additional testing of the subject. The psychological effect of the presence of an accurate noninvasive drug and alcohol testing device in the school or workplace can be a strong positive deterrent to drug use.

BRIEF DESCRIPTION OF DRAWINGS

FIG. 1 shows a typical infrared thermometer configuration, showing the detector, collecting optics and processing electronics necessary to produce a temperature signal and display it on a meter display, FIG. 2 shows a basic diagram of an infrared thermometer that passively detects incoming infrared radiation, processes it through a low-noise preamplifier, and converts it to a digital readout, FIG. 3 is a perspective view of an electric thermometer with parts broken away, and FIG. 4 is a diagrammatical schematic view of the electronic thermometer shown in FIG. 3.

DETAILED DESCRIPTION OF PREFERRED EMBODIMENT

While the practice of the present invention is in the detection of thermal discrepancy of the eyes of a person and its relation to health impairment and/or alcohol and drug abuse, an elementary understanding of instruments for passively detecting and/or measuring eye temperature is desirable.

In 1800 Sir William Herschel, Royal Astronomer to England's King George III, devised a series of experiments, using prisms and sensitive mercury thermometers to determine which colors had the greatest heating effect. As a thermometer was moved from the violet to the red end of the spectrum, the heating effect increased. As the thermometer was moved past the visible red end of the spectrum, even greater heating was observed. The dark heat discovered by Herschel became known as infrared. The first radiation thermometers based on infrared sensors were built in the early 1950's. Since hotter targets radiate more infrared energy than cooler targets, these early instruments sensed changes in hotter targets, above 200 degrees F.

In the past decade highly stable solid state DC amplifier modules with low noise and at low cost have been developed. This resulted in small, compact and rugged infrared sensing heads, with no moving parts, which transmit a DC current proportional to target infrared radiation. It has become increasingly necessary to measure the temperature of materials without contact, especially when the target is physically remote, is in motion, is electrically hazardous, or is so small and fragile that the thermal balance of the target being measured would be upset by contact with temperature measurement devices. Today's infrared thermometers can measure temperatures with sensitivities down to 0.1 degree C. and with response times of milliseconds and faster.

FIG. 1 illustrates a typical infrared radiation thermometer, showing the detector 10, the collecting optics (lens 12 and filter 14), and processing electronics 16 necessary to produce a temperature signal at output 18 and display it on a meter 20. The thermometer is shown aimed at target 22. The target size depends upon its distance 24 from the lens 12 and the lens optical characteristics. Filter 14 determines that part of the infrared spectrum over which the thermometer operates. The detector 10 converts infrared energy into an electrical signal which is conditioned and amplified by electronics circuitry 16 to display detection, measuring, monitering or control information on readout meter 20.

FIG. 2 shows a basic diagram of an infrared thermometer with a sighting system for determining the exact target being measured. Some infrared thermometers use a sighting scope for directing them to specific targets. However, they show the centerpoint of the area being measured, not the diameter. When the target does not use the full target area measured by the thermometer, background surface temperatures are also measured, resulting in erroneous temperature readings. The diagram in FIG. 2 utilizes a pulsating light 25 directed through the infrared optics 28 which illuminates the exact area of temperature measurement. This light presents a true, visible picture of the infrared field of-view at any distance. Since the infrared signal and the light share the same optics, they cannot be knocked out of alignment. They share the same field of view at all distances.

An xenon flash lamp 26 pulses every 0.5 sec. and does not heat the target or alter the reading as a steady light would do. The pulsating light is also easier to see in daylight than a steady light. The outgoing visible light 30 from optical assembly 28 is projected onto the target as the infrared optics 28 collects incoming infrared radiation 32 from the target and focuses it on the thermopile infrared detector 34. Detector 34, in turn, converts the radiation to a proportional electrical signal which is the exact electrical analog of the incoming infrared radiation 32, and hence target temperature. This small electrical signal is then amplified in the low noise amplifier 36 and linearized. After linearization and further conditioning, the analog signal is converted to an equivalent digital signal by analog-to-digital converter 38 which feeds through digital processor chip 40 to drive the digital display 42. With aiming technique improvements, infrared thermometers have become dependable temperature measuring instruments whose accuracy make them useful in precision research applications. An infrared thermometer with an improved target sighting system is disclosed in U.S. Pat. No. 4,494,881 issuing Jan. 22, 1985 to Charles E. Everest for Intra- Optical Light Beam Sighting System for an Infrared Thermometer. That information is incorporated herein by reference.

FIG. 3 is a perspective view with parts broken away of a thermometer having a high-speed pyroelectric infrared sensor for measuring body temperature and a relatively slow speed ambient temperature sensor. For medical use the thermometer detects warm spots on the surface of the skin of a subject under test.

FIG. 4 is a diagrammical schematic view of the thermometer shown in FIG. 3. The thermometer generally designated as 44 comprises a housing 46 forming an interior chamber 48, a barrel or wave guide 50 for directing infrared radiation into the chamber 48, a shutter assembly 52 for controlling the passage of infrared radiation through the barrel 50, a pyroelectric sensor assembly 54, an ambient temperature sensor 56, and an electric circuit 58. The housing 46 has an elongated lower end 60 which forms a pistol grip type handle of convenient size for one hand operation. The upper end 62 of housing 46 forms the interior chamber 48 for mounting the pyroelectric sensor assembly 54 and the ambient temperature sensor 56, and provides a shield to exterior infrared radiation other than that received through the barrel 50. The barrel 50 is mounted to the forward side 64 of housing 46 in alignment with the pyroelectric sensor 54 so as to direct or aim infrared radiation from the object 66 to be measured to the pyroelectric sensor 54 mounted within the chamber 48.

The ambient temperature sensor 56 is mounted within the interior chamber 48 in thermal equilibrium with the pyroelectric sensor 54, barrel 50, and shutter element 68 so as to sense or moniter the internal temperature of the housing 46. The ambient temperature sensor 56 senses the internal temperature of the housing 46 and generates an electrical signal proportional thereto which is applied to the electronic circuit 58 through connector 70. The ambient temperature sensor 56 may be relatively slow-acting as contrasted to the fast-acting pyroelectric sensor 54 and need only have a response time sufficient to track the changes of the internal ambient temperature of the chamber 48.

The shutter assembly 52 comprises a shutter 68, a shutter control mechanism 74, and a manually actuated pushbutton 76. The shutter 72 is operationally mounted at the inner end 78 of the barrel 50 so as to be actuable between a normally closed position closing off the transmission of infrared energy from the barrel 50 to the pyroelectric sensor 54 and an open position permitting infrared energy to pass from the barrel 50 to the pyroelectric sensor 54.

The electronic circuit 58 includes an amplifier circuit 80, a microprocessor or microcontroller 82, a shutter sensor switch 84 and a digital visual display device 86. The microprocessor 82 is interconnected to the ambient temperature sensor 56 through connector 88, the amplifier circuit 80 through connector 90, and the shutter sensor switch 84 and connector 92 to receive electrical input signals indicative of the internal ambient temperature of the housing 46, the actuation of shutter assembly 52, and the temperature differential between the pyrometer sensor 54 and the object to be measured. The microprocessor 82 is of conventional design having suitable data and program memory and being programmed to process the electrical signal from the ambient temperature sensor 56 and the amplified electrical signal from the pyroelectric sensor 54 to calculate the absolute temperature of the object 66 to be measured. Based upon the calculated temperature of the body 66, the microprocessor 82 generates a control signal to drive the display device 86 to visually indicate the calculated temperature. More specifically, the amplitude of the electrical signal generated by the pyroelectric sensor 54 is a nonlinear function of the object 66 to be measured and the temperature of the sensor 56 prior to exposure to the radiation emitted by the object 66, i.e., the difference between the temperature of the object 66 and the ambient temperature of the thermometer. For more information concerning the infrared thermometer in FIGS. 3 and 4 reference is had to U.S. Pat. No. 4,797,840 issuing Jan. 10, 1989 to Jacob Fraden for Infrared Electronic Thermometer and Method for Measuring Temperature. That information is incorporated herein by reference.

With the recent improvements in infrared thermometers in terms of speed, accuracy and convenience, they now are used in medical research. In accordance with the present invention top-of-the-line thermometers may now be used in ophthermology, the science of dealing with eye temperature, being developed by the present inventor. With it, eye temperature norms can be established for one person or an average group of persons. Thereafter a temperature reading in one or both eyes that deviates too far from these norms indicate a problem and a suggestion of further testing since the person under examination may be at risk medically or in a drug and alcohol situation. For example, if one eye has a temperature of 85 degrees F. and the other eye has a temperature of 95 degrees F., the person under test may have a tumor or a carotid artery problem. If the known normal eye temperature is between 89 degrees F. and 91 degrees F., and a motorist registers an elevated temperature in at least one eye of 91.9 degrees F., this could constitute probable cause and the motorist should be further tested for alcohol and drug abuse.

Having revealed the use of ophthermometers (top-of-the-line infrared thermometers) in the new field of ophthermology (the science of dealing with eye temperature) pioneered and being developed by the present inventor, it is to be understood that there are various alternatives to those described, and such deviations and variations from those set forth herein are also considered to be part of this invention.

What I claim is:

1. A method of detecting eye abnormality in a subject due to abnormal blood flow comprising the steps of detecting and measuring temperatures of the eyes of the subject and comparing such temperatures with known temperature norms.

2. A method of detecting eye abnormality in a subject due to abnormal blood flow as set forth in claim 1 comprising the steps of establishing temperature norms for the subject is eye under normal eye blood flow conditions and comparing this temperature with present eye temperatures of said subject.

3. A method of detecting eye abnormality in a subject as set forth in claim 1 due to abnormal blood flow Caused by misfunctioning of the thyroid gland, pain in an eye, infection, regulation of medication, use of alcohol and drugs comprising the steps of taking eye temperatures of the subject and comparing it with established temperature norms for the subject and clinically established temperatures norms.

4. A method of detecting the presence of stimulants and depressives in a person's bloodstream comprising the steps of measuring eye temperatures of the person when the person's bloodstream is known to be free of stimulants and depressives, measuring the person's eye temperatures at a time when such presence is suspect, comparing such temperatures and noting differences in such temperatures.

5. A method of detecting possible arteriosclerotic disease of the extracranial carotid arterial complex comprising measuring the temperatures of each eye of a person and noting any difference between the two temperatures.

6. The method of performing eye surgery comprising the steps of taking the temperature of the impaired eye eye to determine whether blood flow is adequate to permit the surgery, performing the surgery if the blood flow is adequate, and monitoring the eye temperature after the surgery is performed.

* * * * *